US012685810B2

(12) United States Patent
Edwards et al.

(10) Patent No.: US 12,685,810 B2
(45) Date of Patent: Jul. 21, 2026

(54) EVAPORATIVE FLUID MANAGEMENT CANISTER FOR WOUND THERAPY SYSTEM

(71) Applicant: KCI Manufacturing Unlimited Company, Westmeath (IE)

(72) Inventors: Thomas Alan Edwards, San Antonio, TX (US); Benjamin A. Pratt, San Antonio, TX (US); Dominic Nolan, San Antonio, TX (US)

(73) Assignee: KCI Manufacturing Unlimited Company, Westmeath (IE)

( * ) Notice: Subject to any disclaimer, the term of this patent is extended or adjusted under 35 U.S.C. 154(b) by 311 days.

(21) Appl. No.: 18/278,960

(22) PCT Filed: Feb. 21, 2022

(86) PCT No.: PCT/IB2022/051521
§ 371 (c)(1),
(2) Date: Aug. 25, 2023

(87) PCT Pub. No.: WO2022/195377
PCT Pub. Date: Sep. 22, 2022

(65) Prior Publication Data
US 2024/0139404 A1 May 2, 2024

Related U.S. Application Data

(60) Provisional application No. 63/162,146, filed on Mar. 17, 2021.

(51) Int. Cl.
*A61M 1/00* (2006.01)

(52) U.S. Cl.
CPC .............. *A61M 1/98* (2021.05); *A61M 1/912* (2021.05); *A61M 2202/0014* (2013.01);
(Continued)

(58) Field of Classification Search
CPC ... A61F 13/05; A61F 2013/00791; A61J 1/05; A61M 1/982; A61M 1/691; A61M 1/60–75; A61M 1/98
See application file for complete search history.

(56) References Cited

U.S. PATENT DOCUMENTS

| 1,355,846 | A | 10/1920 | Rannells |
| 2,547,758 | A | 4/1951 | Keeling |
| | | (Continued) | |

FOREIGN PATENT DOCUMENTS

| AU | 550575 | B2 | 3/1986 |
| AU | 745271 | B2 | 3/2002 |
| | | (Continued) | |

OTHER PUBLICATIONS

PCT International Search Report/Written Opinion for PCT/IB2022/051521, mailed Apr. 26, 2022.
(Continued)

*Primary Examiner* — Jacqueline F Stephens
*Assistant Examiner* — Meagan Ngo

(57) ABSTRACT

A canister for use with a wound therapy system includes first and second compartments configured to receive and contain wound exudate, and an airflow pathway. The airflow pathway includes a planar region positioned between the first compartment and the second compartment, an inlet extending from a first end of the planar region at an obtuse angle relative to the planar region, an outlet at a second end of the planar region.

20 Claims, 9 Drawing Sheets

(52) U.S. Cl.

CPC .............. *A61M 2202/0028* (2013.01); *A61M 2202/0042* (2013.01); *A61M 2202/005* (2013.01); *A61M 2205/02* (2013.01); *A61M 2205/07* (2013.01); *A61M 2205/126* (2013.01); *A61M 2205/50* (2013.01); *A61M 2205/7527* (2013.01); *A61M 2205/7545* (2013.01); *A61M 2205/8206* (2013.01)

(56) References Cited

U.S. PATENT DOCUMENTS

| | | | |
|---|---|---|---|
| 2,632,443 | A | 3/1953 | Lesher |
| 2,682,873 | A | 7/1954 | Evans et al. |
| 2,910,763 | A | 11/1959 | Lauterbach |
| 2,969,057 | A | 1/1961 | Simmons |
| 3,066,672 | A | 12/1962 | Crosby, Jr. et al. |
| 3,367,332 | A | 2/1968 | Groves |
| 3,520,300 | A | 7/1970 | Flower, Jr. |
| 3,568,675 | A | 3/1971 | Harvey |
| 3,648,692 | A | 3/1972 | Wheeler |
| 3,682,180 | A | 8/1972 | McFarlane |
| 3,826,254 | A | 7/1974 | Mellor |
| 4,080,970 | A | 3/1978 | Miller |
| 4,096,853 | A | 6/1978 | Weigand |
| 4,139,004 | A | 2/1979 | Gonzalez, Jr. |
| 4,165,748 | A | 8/1979 | Johnson |
| 4,184,510 | A | 1/1980 | Murry et al. |
| 4,233,969 | A | 11/1980 | Lock et al. |
| 4,245,630 | A | 1/1981 | Lloyd et al. |
| 4,256,109 | A | 3/1981 | Nichols |
| 4,261,363 | A | 4/1981 | Russo |
| 4,275,721 | A | 6/1981 | Olson |
| 4,284,079 | A | 8/1981 | Adair |
| 4,297,995 | A | 11/1981 | Golub |
| 4,333,468 | A | 6/1982 | Geist |
| 4,373,519 | A | 2/1983 | Errede et al. |
| 4,382,441 | A | 5/1983 | Svedman |
| 4,392,853 | A | 7/1983 | Muto |
| 4,392,858 | A | 7/1983 | George et al. |
| 4,419,097 | A | 12/1983 | Rowland |
| 4,465,485 | A | 8/1984 | Kashmer et al. |
| 4,475,909 | A | 10/1984 | Eisenberg |
| 4,480,638 | A | 11/1984 | Schmid |
| 4,525,166 | A | 6/1985 | Leclerc |
| 4,525,374 | A | 6/1985 | Vaillancourt |
| 4,540,412 | A | 9/1985 | Van Overloop |
| 4,543,100 | A | 9/1985 | Brodsky |
| 4,548,202 | A | 10/1985 | Duncan |
| 4,551,139 | A | 11/1985 | Plaas et al. |
| 4,569,348 | A | 2/1986 | Hasslinger |
| 4,605,399 | A | 8/1986 | Weston et al. |
| 4,608,041 | A | 8/1986 | Nielsen |
| 4,640,688 | A | 2/1987 | Hauser |
| 4,655,754 | A | 4/1987 | Richmond et al. |
| 4,664,662 | A | 5/1987 | Webster |
| 4,710,165 | A | 12/1987 | McNeil et al. |
| 4,733,659 | A | 3/1988 | Edenbaum et al. |
| 4,743,232 | A | 5/1988 | Kruger |
| 4,758,220 | A | 7/1988 | Sundblom et al. |
| 4,787,888 | A | 11/1988 | Fox |
| 4,826,494 | A | 5/1989 | Richmond et al. |
| 4,838,883 | A | 6/1989 | Matsuura |
| 4,840,187 | A | 6/1989 | Brazier |
| 4,863,449 | A | 9/1989 | Therriault et al. |
| 4,872,450 | A | 10/1989 | Austad |
| 4,878,901 | A | 11/1989 | Sachse |
| 4,897,081 | A | 1/1990 | Poirier et al. |
| 4,906,233 | A | 3/1990 | Moriuchi et al. |
| 4,906,240 | A | 3/1990 | Reed et al. |
| 4,919,654 | A | 4/1990 | Kalt |
| 4,941,882 | A | 7/1990 | Ward et al. |
| 4,953,565 | A | 9/1990 | Tachibana et al. |
| 4,969,880 | A | 11/1990 | Zamierowski |
| 4,985,019 | A | 1/1991 | Michelson |
| 5,037,397 | A | 8/1991 | Kalt et al. |

| | | | |
|---|---|---|---|
| 5,086,170 | A | 2/1992 | Luheshi et al. |
| 5,092,858 | A | 3/1992 | Benson et al. |
| 5,100,396 | A | 3/1992 | Zamierowski |
| 5,134,994 | A | 8/1992 | Say |
| 5,149,331 | A | 9/1992 | Ferdman et al. |
| 5,167,613 | A | 12/1992 | Karami et al. |
| 5,176,663 | A | 1/1993 | Svedman et al. |
| 5,215,522 | A | 6/1993 | Page et al. |
| 5,232,453 | A | 8/1993 | Plass et al. |
| 5,261,893 | A | 11/1993 | Zamierowski |
| 5,278,100 | A | 1/1994 | Doan et al. |
| 5,279,550 | A | 1/1994 | Habib et al. |
| 5,298,015 | A | 3/1994 | Komatsuzaki et al. |
| 5,342,376 | A | 8/1994 | Ruff |
| 5,344,415 | A | 9/1994 | DeBusk et al. |
| 5,358,494 | A | 10/1994 | Svedman |
| 5,437,622 | A | 8/1995 | Carion |
| 5,437,651 | A | 8/1995 | Todd et al. |
| 5,527,293 | A | 6/1996 | Zamierowski |
| 5,549,584 | A | 8/1996 | Gross |
| 5,556,375 | A | 9/1996 | Ewall |
| 5,607,388 | A | 3/1997 | Ewall |
| 5,636,643 | A | 6/1997 | Argenta et al. |
| 5,645,081 | A | 7/1997 | Argenta et al. |
| 6,071,267 | A | 6/2000 | Zamierowski |
| 6,135,116 | A | 10/2000 | Vogel et al. |
| 6,241,747 | B1 | 6/2001 | Ruff |
| 6,287,316 | B1 | 9/2001 | Agarwal et al. |
| 6,345,623 | B1 | 2/2002 | Heaton et al. |
| 6,488,643 | B1 | 12/2002 | Tumey et al. |
| 6,493,568 | B1 | 12/2002 | Bell et al. |
| 6,553,998 | B2 | 4/2003 | Heaton et al. |
| 6,814,079 | B2 | 11/2004 | Heaton et al. |
| 7,846,141 | B2 | 12/2010 | Weston |
| 8,062,273 | B2 | 11/2011 | Weston |
| 8,216,198 | B2 | 7/2012 | Heagle et al. |
| 8,251,979 | B2 | 8/2012 | Malhi |
| 8,257,327 | B2 | 9/2012 | Blott et al. |
| 8,398,614 | B2 | 3/2013 | Blott et al. |
| 8,449,509 | B2 | 5/2013 | Weston |
| 8,529,548 | B2 | 9/2013 | Blott et al. |
| 8,535,296 | B2 | 9/2013 | Blott et al. |
| 8,551,060 | B2 | 10/2013 | Schuessler et al. |
| 8,568,386 | B2 | 10/2013 | Malhi |
| 8,679,081 | B2 | 3/2014 | Heagle et al. |
| 8,821,458 | B2 | 9/2014 | Locke et al. |
| 8,834,451 | B2 | 9/2014 | Blott et al. |
| 8,926,592 | B2 | 1/2015 | Blott et al. |
| 9,017,302 | B2 | 4/2015 | Vitaris et al. |
| 9,198,801 | B2 | 12/2015 | Weston |
| 9,211,365 | B2 | 12/2015 | Weston |
| 9,289,542 | B2 | 3/2016 | Blott et al. |
| 2002/0077661 | A1 | 6/2002 | Saadat |
| 2002/0115951 | A1 | 8/2002 | Norstrem et al. |
| 2002/0120185 | A1 | 8/2002 | Johnson |
| 2002/0143286 | A1 | 10/2002 | Tumey |
| 2009/0221990 | A1 | 9/2009 | Jaeb et al. |
| 2009/0306630 | A1* | 12/2009 | Locke ................... A61M 1/784 604/317 |
| 2011/0257613 | A1* | 10/2011 | Locke ................... A61M 1/784 604/319 |
| 2012/0046624 | A1* | 2/2012 | Locke ................... A61M 1/784 604/319 |
| 2013/0053798 | A1* | 2/2013 | Coulthard ............... A61M 1/73 604/319 |
| 2014/0163491 | A1 | 6/2014 | Schuessler et al. |
| 2015/0080788 | A1 | 3/2015 | Blott et al. |
| 2015/0202353 | A1* | 7/2015 | Daughtery .............. A61M 1/98 604/319 |
| 2016/0175500 | A1* | 6/2016 | Cali ...................... A61M 1/912 604/319 |
| 2019/0381220 | A1 | 12/2019 | Locke et al. |

FOREIGN PATENT DOCUMENTS

| | | | |
|---|---|---|---|
| AU | 755496 | B2 | 12/2002 |
| CA | 2005436 | A1 | 6/1990 |
| DE | 2640413 | A1 | 3/1978 |

(56)　　　　　　References Cited

FOREIGN PATENT DOCUMENTS

| DE | 4306478 | A1 | 9/1994 |
|---|---|---|---|
| DE | 29504378 | U1 | 9/1995 |
| EP | 0100148 | A1 | 2/1984 |
| EP | 117632 | A2 | 9/1984 |
| EP | 161865 | A2 | 11/1985 |
| EP | 358302 | A2 | 3/1990 |
| EP | 1018967 | A1 | 7/2000 |
| GB | 692578 | A | 6/1953 |
| GB | 2195255 | A | 4/1988 |
| GB | 2197789 | A | 6/1988 |
| GB | 2220357 | A | 1/1990 |
| GB | 2235877 | A | 3/1991 |
| GB | 2329127 | A | 3/1999 |
| GB | 2333965 | A | 8/1999 |
| JP | 4129536 | B2 | 8/2008 |
| SG | 71559 | | 4/2002 |
| WO | 80/02182 | A1 | 10/1980 |
| WO | 8704626 | A1 | 8/1987 |
| WO | 90010424 | A1 | 9/1990 |
| WO | 93009727 | A1 | 5/1993 |
| WO | 94020041 | A1 | 9/1994 |
| WO | 9605873 | A1 | 2/1996 |
| WO | 9718007 | A1 | 5/1997 |
| WO | 9913793 | A1 | 3/1999 |

OTHER PUBLICATIONS

Louis C. Argenta, MD and Michael J. Morykwas, PhD; Vacuum-Assisted Closure: A New Method for Wound Control and Treatment: Clinical Experience; Annals of Plastic Surgery; vol. 38, No. 6, Jun. 1997; pp. 563-576.

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, p. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96.

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164.

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union

(56)  References Cited

OTHER PUBLICATIONS

Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians; Jul. 2007.

* cited by examiner

| Description | Inlet Pressure (Pa) | Mean Surface Velocity (m/s) | Mean Surface Velocity (m/s) | Exit Volumetric Flow Rate (m³h) |
|---|---|---|---|---|
| Data | 609 | 1.3 | 12.55 | 5.43 |

EVAPORATIVE FLUID MANAGEMENT CANISTER FOR WOUND THERAPY SYSTEM

CROSS-REFERENCE TO RELATED APPLICATIONS

This application claims the benefit of priority to U.S. Provisional Application No. 63/162,146, filed on Mar. 17, 2021, which is incorporated herein by reference in its entirety.

BACKGROUND

The present disclosure relates generally to negative pressure wound therapy (NPWT) systems. More particularly, the present disclosure relates to active or forced evaporation at a canister of the NPWT system.

SUMMARY

One implementation of the present disclosure is a canister for use with a wound therapy system. The canister includes first and second compartments configured to receive and contain wound exudate, and an airflow pathway. The airflow pathway includes a planar region positioned between the first compartment and the second compartment, an inlet extending from a first end of the planar region at an obtuse angle relative to the planar region, an outlet at a second end of the planar region.

In some embodiments, the first compartment is separated from the airflow pathway by a first filter configured to allow water molecules to pass from the first compartment to the airflow pathway and prevent contaminants from passing from the first compartment to the airflow pathway. The first filter may include a polyurethane film. The canister may include a rigid structure defining the first and second compartments and formed of a thermoplastic polyurethane resin. The canister of claim 4, wherein the rigid structure is ultrasonically welded to the polyurethane film.

In some embodiments, the first filter includes a film having a high moisture vapor transmission rate. For example, the high moisture vapor transmission may be in a range between 2000 and 5000 g/m²/day.

In some embodiments, the inlet is cylindrical. The inlet may be formed to match a cross-sectional shape of a fan. The inlet may widen proximate the planar region to reduce turbulence and back-pressure in the airflow pathway.

In some embodiments, the canister includes a curved wall providing a smooth transition from the inlet to the planar region. In some embodiments, the obtuse angle is in a range between 130 degrees and 150 degrees. In some embodiments, the inlet has a screw-type form configured to provide rotation of airflow therethrough.

Another implementation of the present disclosure is a therapy system. The therapy system includes a dressing configured to be sealed over a wound site, a negative pressure source configured to draw a negative pressure at the dressing and cause wound exudate to move out of the dressing, and a canister configured to be placed in fluid communication with the dressing. The canister includes first and second compartments configured to receive and retain the wound exudate from the dressing and an airflow pathway. The airflow pathway includes a planar region positioned between the first compartment and the second compartment, an inlet extending from a first end of the planar region at an obtuse angle relative to the planar region, and an outlet at a second end of the planar region. The therapy system also includes an air mover aligned with the inlet and configured to force air through the airflow pathway to facilitate transfer of moisture from the wound exudate out of the first and second components.

In some embodiments, the air mover is an axial fan, a blower, or a centrifugal fan. In some embodiments, the therapy system further includes a housing and the air mover and the negative pressure source are installed in the housing. The canister is configured to be selectively and removeably coupled to the housing. The therapy system may include a battery installed in the housing. The canister is configured to be selectively and removeably coupled to the housing.

In some embodiments, the therapy system also includes a controller configured to control the air mover to operate in a pulsing pattern.

In some embodiments, the therapy system also includes tubing connecting the dressing to the canister. The first and second compartments may be separated from the airflow pathway by a film material configured to allow water molecules to pass from the first and second compartments to the airflow pathway and prevent contaminants from passing from the first and second compartments to the airflow pathway.

Another implementation of the present disclosure is a method of manufacturing a canister for a wound therapy device. The method includes providing first and second rigid structures formed of a polyurethane resin, providing first and second filters formed of a polyether urethane film, ultrasonically welding the first rigid structure to the first filter, ultrasonically welding the second rigid structure to the second filter, and ultrasonically welding the first rigid structure to the second rigid structure such that a planar airflow pathway is defined between the first filter and the second filter.

In some embodiments, the method includes coupling a first wall to the first rigid structure such that a first compartment is defined by the first wall, the first rigid structure, and the first filter. The method may also include coupling a second wall to the second rigid structure such that a second compartment is defined by the second wall, the second rigid structure, and the second filter.

In some embodiments, the method includes configuring the second rigid structure to define an inlet extending from the planar airflow pathway and across the second rigid structure. The method may also include forming the first and second filters such that the first and second filters are configured to allow water molecules to pass across the first and second filters.

Those skilled in the art will appreciate that the summary is illustrative only and is not intended to be in any way limiting. Other aspects, inventive features, and advantages of the devices and/or processes described herein, as defined solely by the claims, will become apparent in the detailed description set forth herein and taken in conjunction with the accompanying drawings.

DETAILED DESCRIPTION

Figure 1:
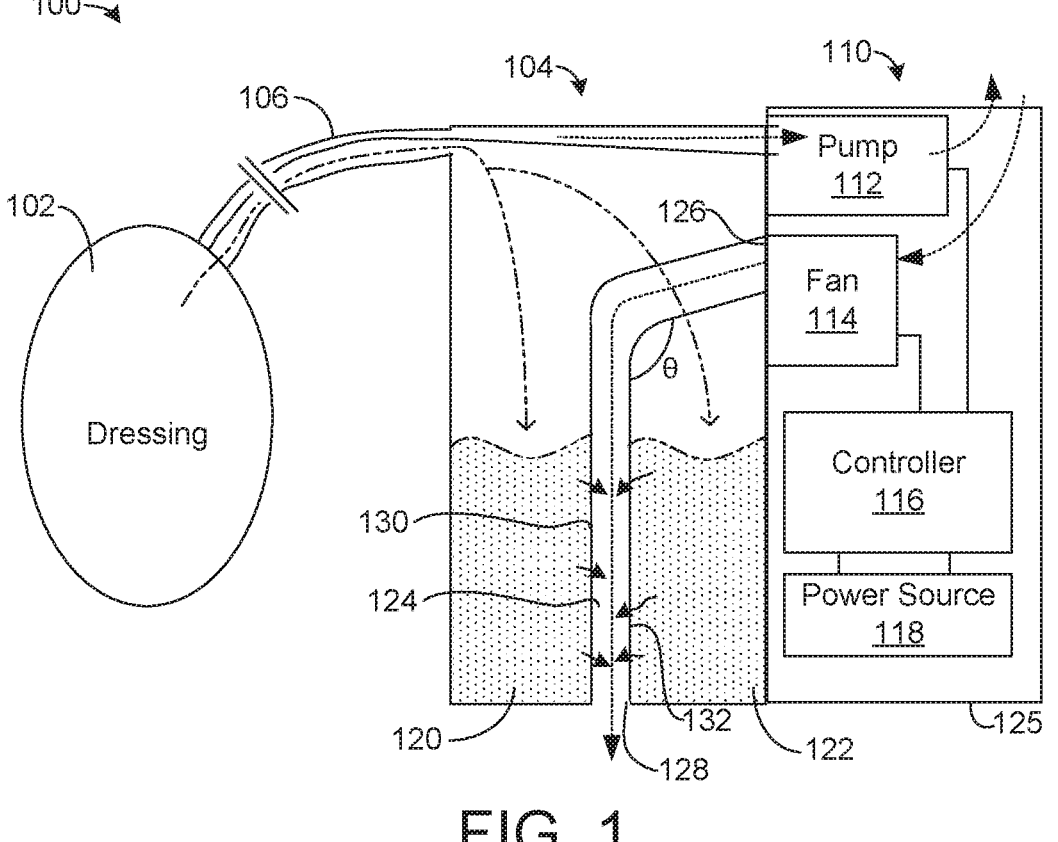
FIG. 1 is a diagram of a wound therapy system, according to an example embodiment.

Referring now to FIG. 1, a wound therapy system 100 is shown, according to some embodiments. Wound therapy system 100 is configured to draw a negative pressure at a wound, collect fluid or wound exudate from the wound at a canister, and provide for enhanced evaporation of the fluid from the canister to the atmosphere. Wound therapy system 100 can be the similar to or incorporate any of the features of the systems of U.S. Pat. No. 8,821,458, filed Apr. 12, 2011, U.S. Pat. No. 8,604,265, filed Apr. 12, 2011, U.S. Pat. No. 9,023,002, filed Apr. 9, 2012, or U.S. Pat. No. 9,433, 711, filed Nov. 12, 2012, the entire disclosures of which are incorporated by reference herein.

Wound therapy system 100 includes a dressing 102, a canister (container, tank, vessel, etc.) 104 configured to be connected to the dressing 102 via tubing 106, and a therapy device 110 configured to be coupled to the canister 104. The therapy device 110 is shown as including a pump 112, a fan 114, a controller 116, and a power source 118.

The dressing 102 is configured to be sealed to a patient's anatomy, for example over a wound of the patient, creating a substantially airtight seal between the patient's anatomy and the dressing 102. The dressing 102 includes an airtight external drape layer which provides the seal, and a manifolding layer (e.g., open-cell foam) between the external layer and the patient which is configured to communicate air pressure to the patient (e.g., to a wound) and to allow for fluid (e.g., wound exudate) to flow away from the wound. The dressing may be the same as or similar to a PRE-VENA™ dressing by KCI and/or a V.A.C.® GRANUFOAM™ dressing by KCI in various embodiments.

The tubing 106 is configured to connect the dressing 102 to the canister 104 and the therapy device 110. The tubing 106 can include multiple lumens. The tubing 106 is configured to provide for the flow of air and wound exudate out of the dressing and to the canister 104 when the therapy device 110 is operated.

The therapy device 110 is shown as including a negative pressure source (shown as pump 112), a fan 114, a controller 116, and a power source 118. The pump 112 is in fluid communication with the tubing 106 (e.g., via the canister 104) such that the pump 112 can be operated to create pressure differential which pulls air, wound exudate, and/or other fluid or contaminants through the tubing 106 from the dressing 102 toward the canister 104. As air is removed from the dressing 102, a negative pressure (relative to atmospheric pressure) is established at the dressing 102 and a wound or other anatomical feature covered by the dressing 102. The wound therapy system 100 can thereby facilitate wound healing by applying negative pressure to a wound.

Wound exudate (e.g., blood, tissues, excretions, other contaminants) can be displaced from the wound by the negative pressure and the pressure differential created by the pump 112. In particular, operation of the pump 112 can draw wound exudate through the tubing 106 to the canister 104. The wound exudate can include fluid, including water with various particles, contaminants, etc. therein. Removing wound exudate from the wound and the dressing 102 can facilitate wound healing, for example by reducing a risk of maceration of a periwound area and extend the duration for which the dressing 102 can be affixed to the patient.

The canister 104 is configured to receive and retain the wound exudate drawn out of the dressing 102 via the tubing 102. In the embodiments herein, the canister 104 is configured to retain the wound exudate while also providing for evaporation of water molecules from the canister 104 to an ambient environment (e.g., to the atmosphere), as described in detail below.

In FIG. 1, the canister 104 is shown as including a first compartment (chamber) 120 and a second compartment (chamber) 122 configured to retain wound exudate received via the tubing 102. The first compartment 120 and the second compartment 122 are at least partially separated by an airflow pathway 124. As shown in FIG. 1, the airflow pathway 124 extends from an inlet 126 to an outlet 128. When the canister 104 is coupled to the therapy device 110, the inlet 126 is aligned with the fan 114.

The airflow pathway 124 is at least partially defined by a first wall 130 of the first chamber 120 and a second wall 132 of the second chamber 122. As described in detail below, the first wall 130 and the second wall 132 are formed as membranes (films, filters, etc.) which allow water molecules to pass therethrough and evaporate into the airflow pathway 124, while also preventing contaminants (e.g., particles, debris, cellular matter, pathogens, oils, other non-water elements) retained by the canister 104 from crossing the first wall 130 and the second wall 132. The airflow pathway 124 is thereby configured to receive water molecules which evaporate into the airflow pathway 124 as air flows through the airflow pathway 124.

The fan 114 can be aligned with the airflow pathway 124 and operated force (e.g., push, blow, etc.) air through the airflow pathway 124. In the embodiment shown in FIG. 1, the fan 114 is configured to pull air from the ambient air and push the air into the airflow pathway 124 via the inlet 126, thereby forcing air to flow from the inlet 126 proximate the fan to the outlet 128 at an opposing end of the first wall 130 and the second wall 132. In other embodiments, the fan 114 pulls air through the airflow pathway 124 in the opposite direction. The fan 114 may be an axial fan driven by an electric motor. In other embodiments, other types of air movers are used (e.g., blowers, centrifugal fans).

By blowing air through the airflow pathway 124 and along the first wall 130 and the second wall 132, the fan 114 actively enhances the amount of water which evaporates from the first chamber 120 and second chamber 122 into the airflow pathway 124. The amount of evaporation may be influenced by the rate of airflow through the airflow pathway 124, as well as by other traits of the airflow (e.g., turbulence, pressure). These factors also effect the energy consumption and efficiency of the fan 114. Accordingly, as described in detail below, the airflow pathway can be designed to increase a rate of evaporation of water from the canister 104 while also reducing energy consumption of the fan 114.

The fan 114 is configured to draw power from the power source 118. The power source 118 may be a battery, for example a rechargeable battery, included onboard the therapy device 110 (e.g., inside a housing 125 which also holds the pump 112 and the fan 114). Accordingly, reducing energy consumption of the fan 114 may advantageously increase the battery life of the therapy device 110 (i.e., the amount of time the therapy device 110 can operate without being recharged). In other embodiments, the power source 118 is provided in the therapy device 110 as circuitry configured to draw power from an electric outlet via a power cord. The power source 118 is also configured to provide electrical power to the pump 112 in the example of FIG. 1.

In the example of FIG. 1, the controller 116 is configured to control the fan 114 and the pump 112. The controller 116 can control the pump 112 to establish and maintain a negative pressure at the dressing 102. The controller 116 can control the fan 114 to operate to force air through the airflow pathway 124 to facilitate evaporation. The controller can provide the fan 114 with an operating pattern which seeks to find an optimal balance between energy consumption of the fan 114 and evaporation of fluid from the canister 104. For example, the controller may cycle the fan 114 between on and off states to reduce power consumption of the fan 114. As another example, the controller may vary the fan speed of the fan 114 (e.g., by varying a voltage provided to the fan) in order to reduce power consumption (as compared to constant operation at full speed) and to create variations in the airflow which may help to enhance the evaporation rate.

FIG. 1 thereby illustrates that the wound therapy system 100 is configured to establish and maintain a negative pressure at the dressing 102 to provide negative pressure therapy to a wound, collect wound exudate in the canister 104, and actively enhance evaporation of water from the wound exudate in the canister 104. Due to this evaporation of water from the canister 104, the canister 104 is kept below its maximum capacity for significantly longer than in embodiments where evaporation is not facilitated. Features which improve the rate of evaporation increase the time over which the wound therapy system 100 can be used without a need to empty or replace the canister 104. In some cases, the wound therapy system 100 is configured to provide a sufficient amount of evaporation to prevent the capacity of the canister 104 from being reached during a typical duration for treatment of a wound using the wound therapy system 100. Various features that provide for enhanced, energy-efficient evaporation of water from the canister 104, and features that facilitate manufacturing of the canister 104, are described in detail below with reference to FIGS. 2-10.

Figure 2:
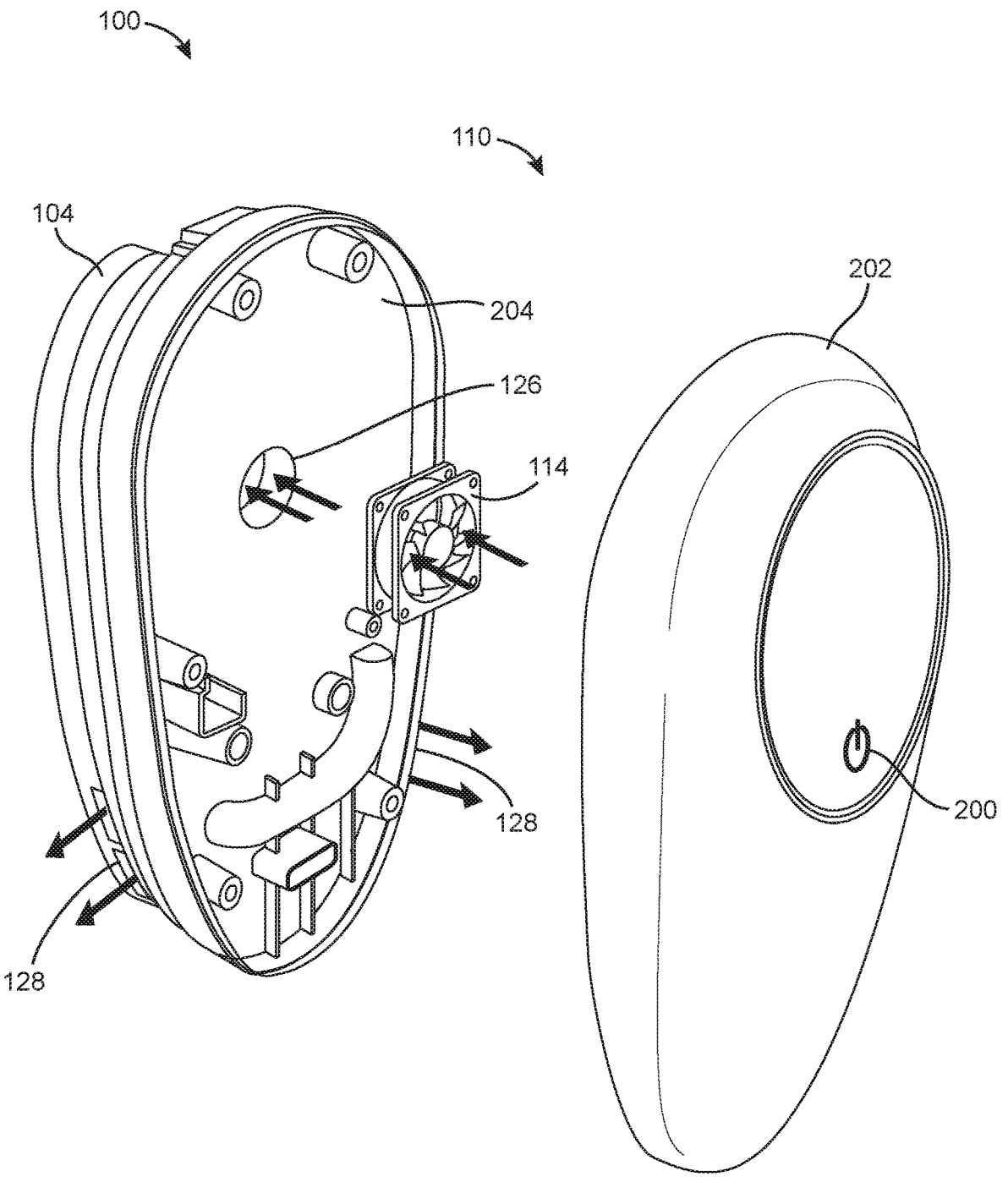
FIG. 2 is a perspective exploded view of a portion of the wound therapy system of FIG. 1, according to an example embodiment.

Referring now to FIG. 2, an exploded perspective view of the canister 104 and the therapy device 110 is shown, according to an exemplary embodiment. In particular, the therapy device 110 is shown in an exploded view so that a position of the fan 114 in the therapy device 110 can be seen. As shown in FIG. 2, the fan 114 is arranged between a first shell 202 and a second shell 204 which couple together to form the housing of the therapy device 110.

The fan 114 is positioned to align with the inlet 126 of the airflow pathway of the canister 104. In the example shown, the fan 114 is an axial fan having an axis oriented perpendicular to the longitudinal axis of the canister 104, such that a surface of the fan is parallel to and can mate with the wall of the second shell 204 of the housing of the therapy device

110 over the inlet 126. The fan 114 is thereby arranged to blow air in a direction perpendicular to the longitudinal axis.

FIG. 2 also shows that outlets 128 of the airflow pathway 124 are spaced apart from the inlet 126 in a longitudinal direction relative to the inlet 126. As a result, the airflow pathway 124 extends in a direction which is at least partially misaligned from the axis of the fan 114. Airflow from the fan 114 through the canister 104 thus changes directions at least once between the inlet 126 and the outlet 128. This change in direction can create back-pressure, turbulence, airflow rate, etc. which can affect energy consumption of the fan and the rate of evaporation into the airflow pathway 1204. Accordingly, enhanced design of the airflow pathway between the fan 114 and the outlets 128 can provide advantages for enhanced evaporation and more efficient fan operation, as described in detail below.

FIG. 2 also shows that the therapy device 110 can include a user input panel 200 positioned on an external surface of the first shell 202 of the housing of the therapy device 110. The user input panel 200 can include one or more buttons that allow a user to input requests to change operation of the therapy device 110. For example, the user input panel 200 can be configured to provide a signal to the controller 116 indicative of a user request to turn on or off the fan 114 and/or the pump 112. In some embodiments, the user input panel 200 allows a user to select an operating mode for the fan 114, for example a power level, a fan speed, a control routine from multiple selectable control routines, a maximum evaporation mode, an energy-efficient mode, etc. In such embodiments, the controller 116 is configured to control the fan 114 to provide the user-requested operation of the fan 114.

Figure 3:
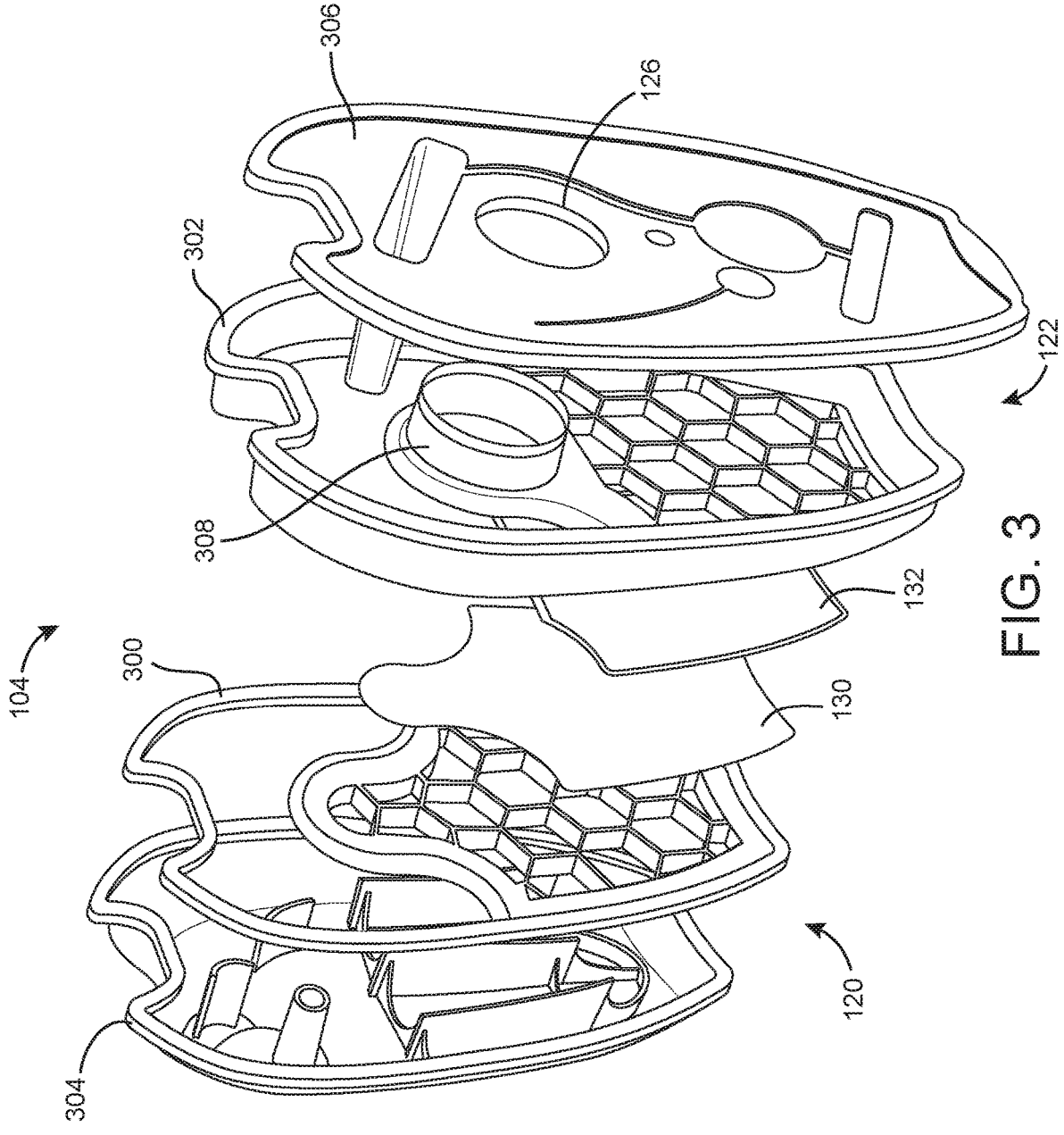
FIG. 3 is an exploded view of a canister of a wound therapy system, according to an example embodiment.

Referring now to FIG. 3, an exploded view of the canister 104 is shown, according to an example embodiment. The canister 104 is shown as including the first wall (first membrane) 130 and the second wall (second membrane) 132 positioned between a first rigid support piece 300 and a second rigid support piece 302. The canister 104 is also shown as including a first outer shell 304 positioned opposite a second outer shell 306 such that the first rigid support piece 300 and the second rigid support piece 302 are arranged between the first outer shell 304 and the second outer shell 306. The first outer shell 304, the first rigid support piece 300, and the first membrane 130 combine to define the first chamber 120 of the canister 104, while the second outer shell 306, the second rigid support piece 302, and the second membrane 132 combine to form the second chamber 122 of the canister 104.

The first rigid support piece 300 is configured to provide a substantially rigid support structure to support the first membrane 130. The first membrane 130 may be made of a relatively thin, flexible material. As shown in FIG. 3, the first rigid support piece 300 includes a honey-comb-type structure of adjacent open hexagons configured to be coupled to the first membrane 130 to provide structural support to the first membrane 130 while also leaving a high percentage of the surface area of the first membrane 130 exposed to an interior of the first chamber 120. The first rigid support piece 300 also includes other surfaces, edges, etc. to provide an interior structure of the canister 104 and join the first rigid support piece 300 and the first membrane 130 to other elements of the canister 104.

The second rigid support piece 302 is configured to provide a substantially rigid support structure to support the second membrane 132. The second membrane 132 may be made of a relatively thin, flexible material. As shown in FIG. 3, the second rigid support piece 302 includes a honeycomb-type structure of adjacent open hexagons configured to be coupled to the second membrane 132 to provide structural support to the second membrane 132 while also leaving a high percentage of the surface area of the second membrane 132 exposed to an interior of the second chamber 122. The second rigid support piece 302 also includes other surfaces, edges, etc. to provide an interior structure of the canister 104 and join the second rigid support piece 302 and the first membrane 130 to other elements of the canister 104.

The first outer shell 304 is configured to define an exposed outer surface of the canister 104, while the second outer shell 306 is configured to define an outer surface of the canister 104 which mates against the housing 125 of the therapy device 110. The second outer shell 306 includes the inlet 126 is provided in for alignment with the fan 114. The second rigid support piece 302 includes a substantially-cylindrical portion 308 of the airflow pathway 124. The cylindrical portion 308 extends across (through) the second rigid support piece 302 from the inlet 126 of the second outer shell 306 to a space between the first membrane 130 and the second membrane 132. As illustrated in detail in FIG. 6, the space between the first membrane 130 and the second membrane 132 defines a substantially planar portion 600 of the airflow pathway 124.

In some embodiments, the first outer shell 304, the first rigid support piece 300, the first membrane 130, the second membrane 132, the second rigid support piece 302, and the second outer shell 306 are ultrasonically welded together to form the canister 104. In particular, in the example shown in FIG. 1, the first membrane 130 is ultrasonically welded directly to the first rigid support piece 300, which is ultrasonically welded directly to the first outer shell 304 and to the second rigid support piece 302. The second membrane 132 is ultrasonically welded directly to the second rigid support piece 302. The second rigid support piece 302 is ultrasonically welded directly to the second outer shell 306.

To facilitate ultrasonic welding of the components of the elements of the canister 104, compatible materials are selected. For example, the first membrane 130 and the second membrane 132 may be made of a polyether urethane film, while the structural components (the first outer shell 304, the first rigid support piece 300, the second rigid support piece 302, and the second outer shell 306) are made of a thermoplastic polyurethane resin, for example a poly-ester-based thermoplastic polyurethane. The thermoplastic polyurethane resin provides a substantially-rigid structure, while the polyether urethane film provides evaporation and moisture transfer properties described below. The materials are compatible such that ultrasonic welding of the materials to one another can be accomplished efficiently and reliably.

The first membrane 130 and the second membrane 132, formed of the polyether urethane film, have a high a water (moisture) vapor transmission rate (MVTR), for example an MVTR in a range between approximately 2000 g/m²□day and approximately 5000 g/m²/day (e.g., approximately 4500 g/m²□day) when measured at 38° C. and 90% relative humidity in an Upright Cup Test. The polyether urethane film may have a thickness between approximately 15 μm and approximately 100 μm, for example between approximately 20 μm and approximately 30 urn.

Figure 5:
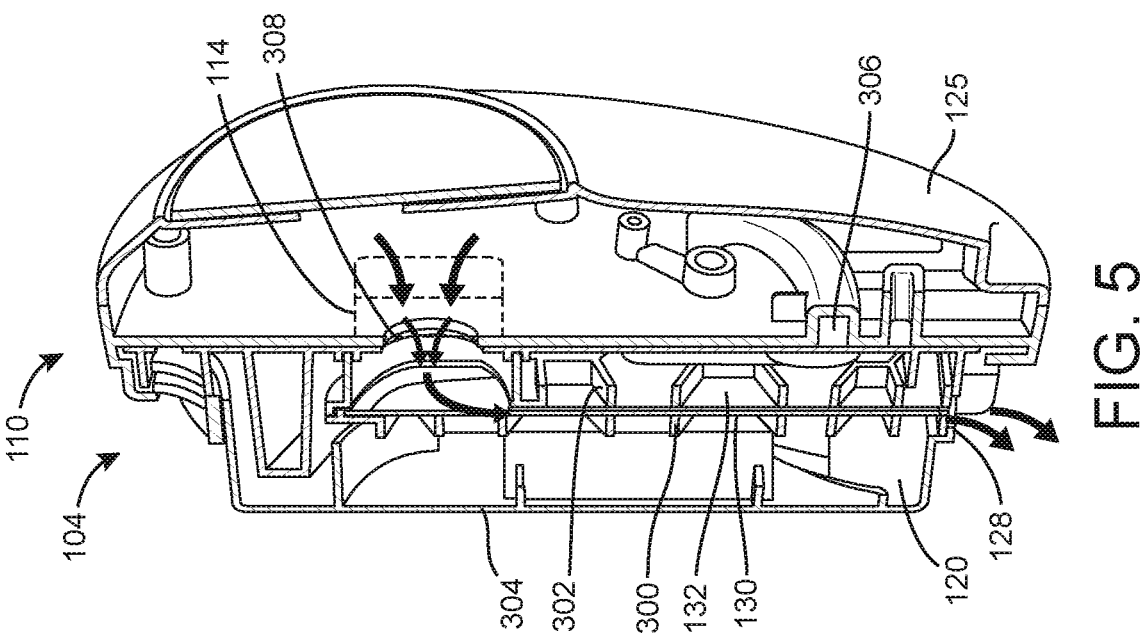
FIG. 5 is a cut-away perspective view of a wound therapy system, according to an example embodiment.
Figure 4:
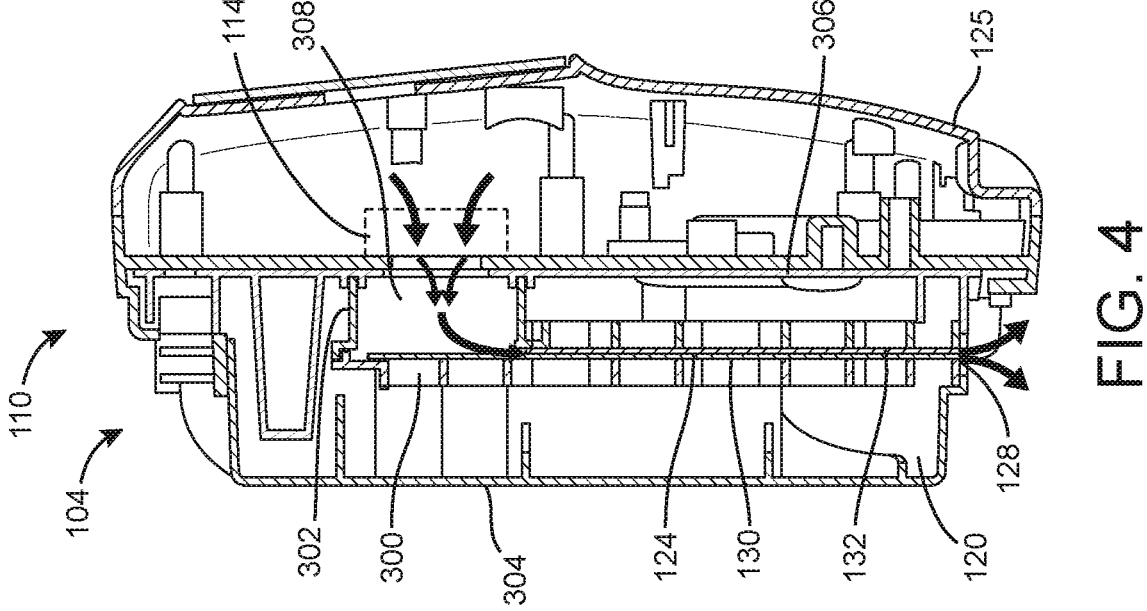
FIG. 4 is a cut-away side view of a portion of a wound therapy system, according to an example embodiment.

Referring now to FIGS. 4-5, cut-away views of the canister 104 and therapy device 110 are shown, according to an example embodiment. As shown in FIGS. 4-5, wound exudate is retained in the canister 104 and the fan 114 is being operated to force air through the canister 104 to actively enhance evaporation of water molecules from the wound exudate in order to reduce the volume of wound exudate stored in the canister 104.

FIG. 4 shows a point in time where the canister 104 is nearly full, i.e., the amount of wound exudate in the canister 104 is nearly at the maximum capacity of the canister 104. The fan 114 is being operated to force air through the airflow pathway 124 and to enhance evaporation of water molecules from the wound exudate retained in the canister 104 into the airflow pathway 124. Water molecules are transmitted across the first membrane 130 and the second membrane 132 and blown out of the outlet 128 as water vapor. Over time, the amount of water stored in the canister 104 is reduced significantly.

FIG. 5 shows a point in time after the fan 114 has been operated over a duration of time sufficient to provide a significant amount of evaporation of water from the canister into the ambient environment. As compared to FIG. 4, the level of wound exudate in FIG. 5 is much lower (e.g., not near a maximum capacity of the canister 104) Enhanced evaporation provided by the teachings herein can cause the amount of wound exudate to be driven down to and/or maintained at a low level as shown in FIG. 5, in some cases. In various applications and situations (different wounds, different composition of wound exudate, different ambient conditions, etc.) the amount of evaporation and the rate of accumulation or rate of reduction of wound exudate volume in the canister 104 will vary.

Figure 6:
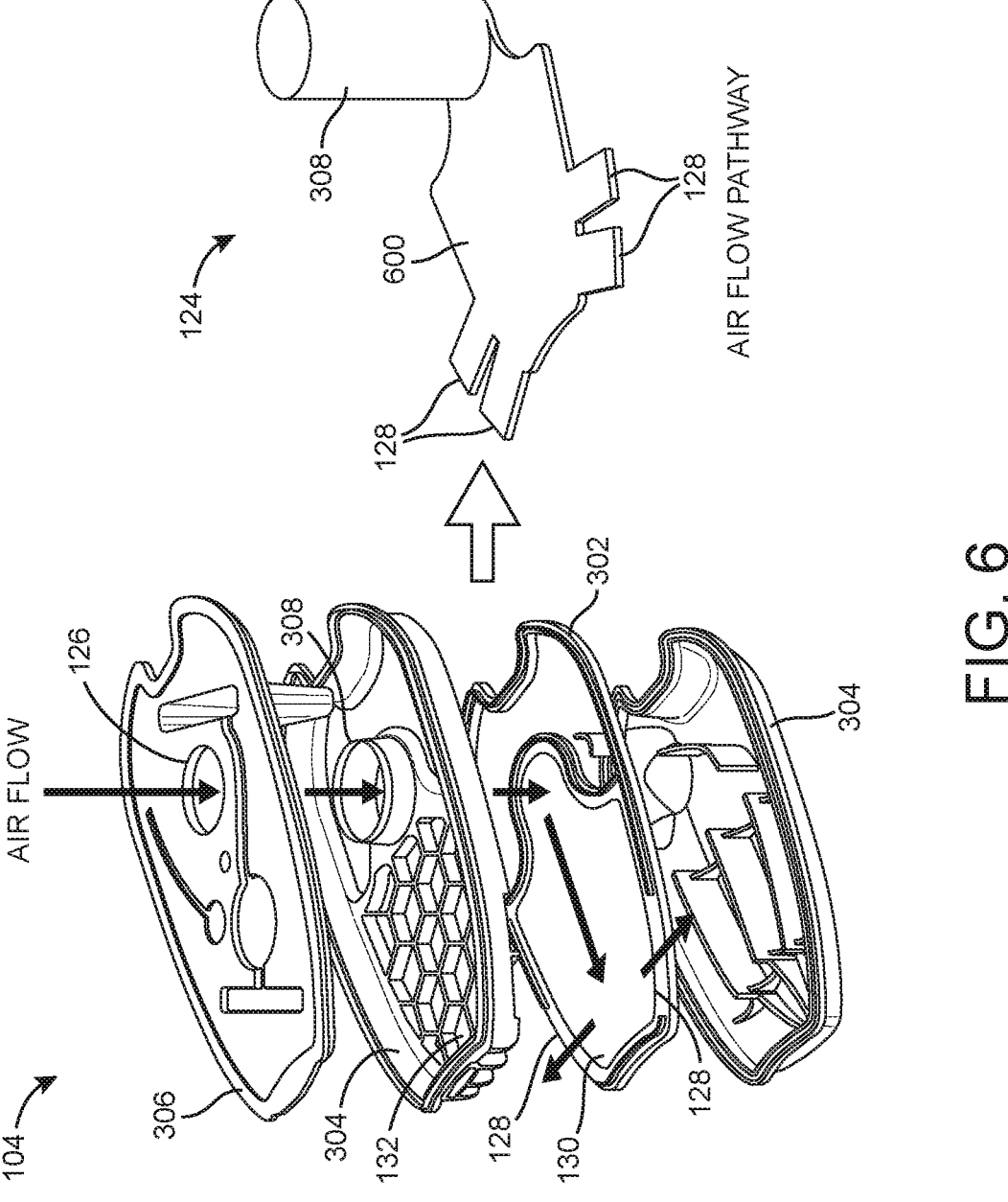
FIG. 6 is an illustration showing an airflow pathway through a canister of a wound therapy system, according to an example embodiment.

Referring now to FIG. 6, an illustration of the airflow pathway 124 in the examples of FIGS. 2-5 is shown, according to an example embodiment. FIG. 6 includes a cut-away view of the canister 104, consistent with the description above. FIG. 6 also includes a perspective view of the airflow pathway 124 isolated from the depiction of the canister 104. Based on the physical structure of the canister 104, the airflow pathway is provided with a planar portion 600 and a cylindrical portion 308 extending from the planar portion 600. The planar portion 600 is defined as a space between the first membrane 130 and the second membrane 132. The cylindrical portion 308 extends from the planar portion 600 to the inlet 126. The fan 114 proximate the inlet 126 can thus blow air directly along the cylindrical portion 308 until the air reaches the planar portion 600, where it is then redirected along the planar portion to the outlets 128

In the example of FIG. 6, the cylindrical portion 308 of the airflow pathway 124 is perpendicular to the planar portion 600. The change-in-direction of the airflow at the intersection between the cylindrical portion 308 and the planar portion 600 may create back-pressure and turbulence, which may restrict airflow as described with reference to FIG. 7 below. In order to improve the flow of air between the cylindrical portion 308 and the planar portion 600 (e.g., to reduce back-pressure, to reduce turbulence, to increase airflow per unit of fan energy consumption), the airflow pathway 124 can be modified as shown below in FIGS. 8 and 9. As discussed below, in various embodiments a curved surface is provided between the cylindrical portion 308 and the planar portion 600 to smooth the transition therebetween by widening the cylindrical portion 308 proximate the planar portion 600 and removing or reducing a sharp angle between the wall of the cylindrical portion 308 and the planar portion 600. This may be provided with the cylindrical portion 308 still at an approximately right angle to the planar portion 600 (as shown in FIG. 8, described below). In other embodiments, the cylindrical portion 308 is rotated relative to the planar portion 600 so that an obtuse angle (in a range between 90 degrees and 180 degrees) is formed between the planar portion 600 and the cylindrical portion 308, thereby reducing the change in direction of the airflow which occurs at the intersection between the cylindrical portion 308 and the planar portion 600 (as shown in FIG. 9, described below).

Figure 7:
FIG. 7 is a combination of graphical representations of airflow through the airflow pathway of a canister of a wound therapy system, according to an example embodiment.
Figure 8:
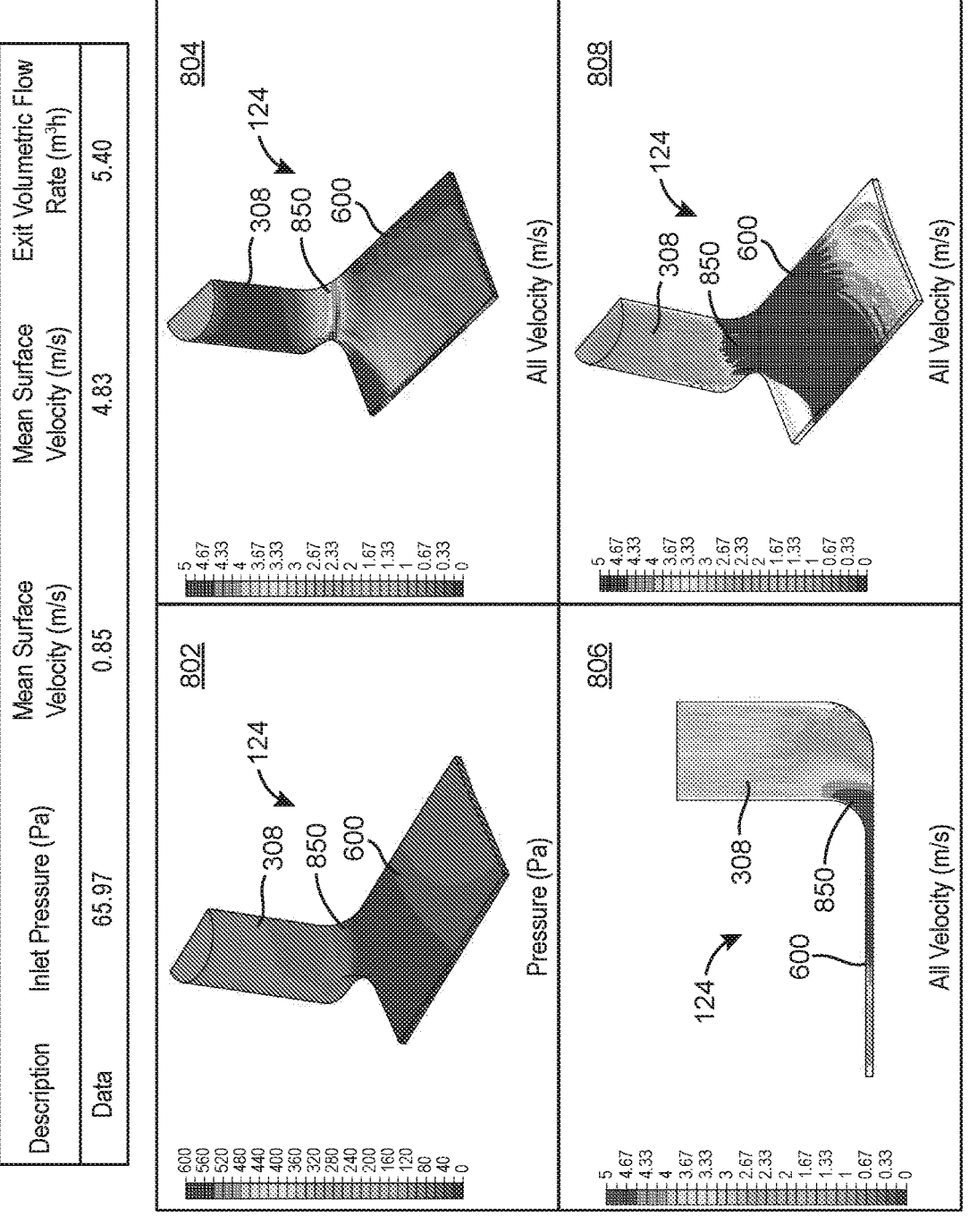
FIG. 8 is combination of graphical representations of airflow through the airflow pathway of another canister of a wound therapy system, according to an example embodiment.
Figure 9:
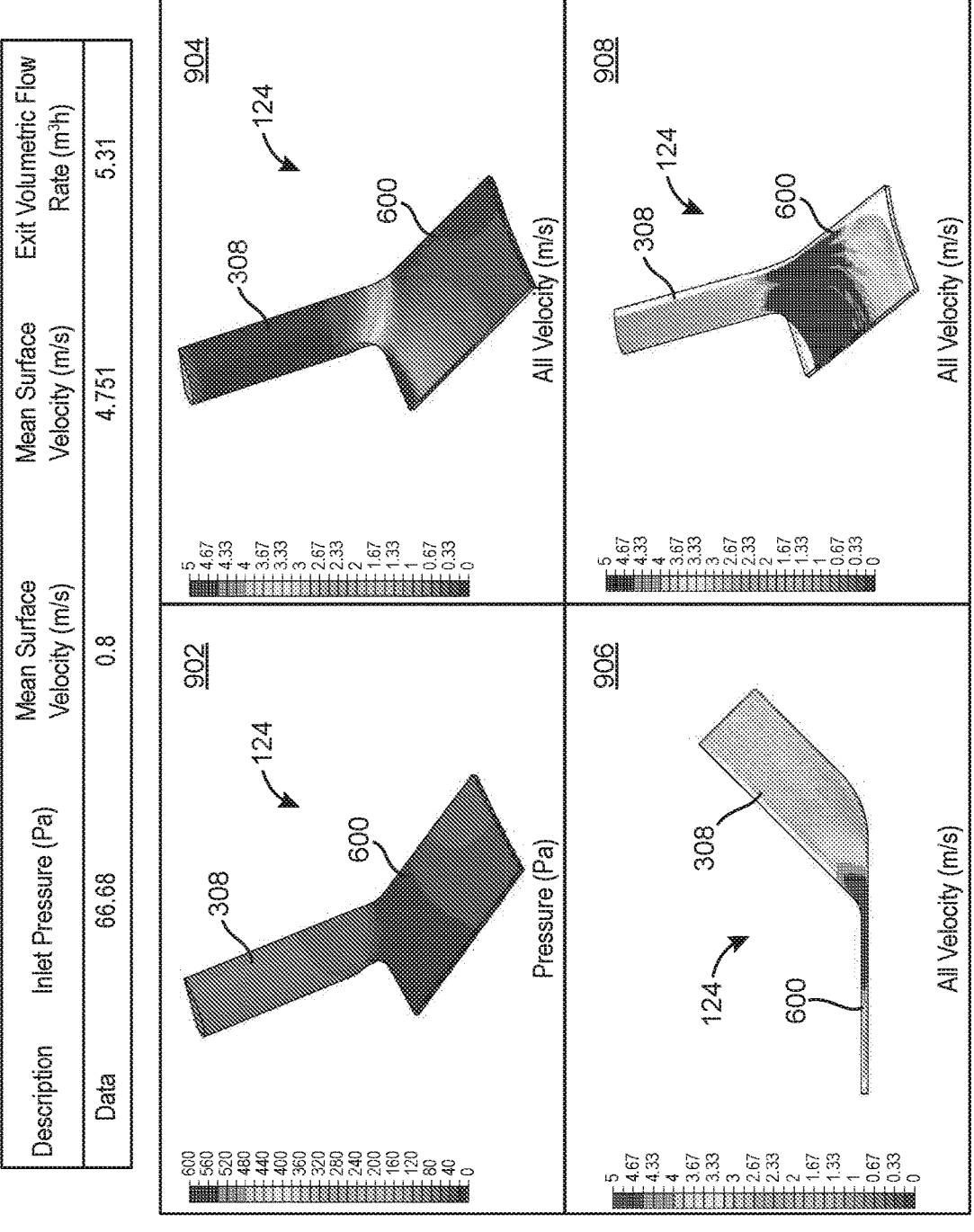
FIG. 9 is combination of graphical representations of airflow through the airflow pathway of yet another canister of a wound therapy system, according to an example embodiment.

Referring now to FIGS. 7-9, graphical depictions of experimental results for example airflow experiments or simulations for different embodiments of the airflow pathway 124 are shown. FIG. 7 shows the airflow pathway 124 in an embodiment consistent with the illustration of FIG. 6, FIG. 8 shows the airflow pathway 124 with a curved surface added to provide as smoothed transition between the cylindrical portion 308 and the planar portion 600, and FIG. 9 shows the cylindrical portion 308 rotated to open an obtuse angle between the cylindrical portion 308 and the planar portion 600. FIGS. 7-9 depict half of the airflow pathway 124 for simplicity, with the understanding that the airflow pathway 124 and the behavior of airflow therethrough is substantially symmetrical. The example experimental results illustrated in FIGS. 7-9 allow for comparison between these embodiments. The data shown is provided for example purposes only and may vary for various embodiments of the therapy system 100 and for various fan speeds, etc.

FIG. 7 shows a table 700, a pressure view 702 of air pressure in the airflow pathway 124, an airflow velocity view 704 showing the velocity of airflow through the airflow pathway 124, a turbulence side view 706 showing turbulence in the airflow pathway 124 from a side view of the airflow pathway 124, and a turbulence perspective view 708 showing turbulence in the airflow pathway 124 from a perspective view.

The table 700 indicates the inlet pressure, mean surface velocity, mean exit velocity, and exit volumetric flow rate for the embodiment of the airflow pathway 124 shown in FIG. 7. The pressure view 702 shows that a high pressure is created in the cylindrical portion 308 by operation of the fan 114, due to the restriction on the airflow at the intersection between the planar portion 600 and the cylindrical portion 308. The pressure in the planar portion 600 is substantially lower than in the cylindrical portion 308. The high pressure in the cylindrical portion 308 may cause an increase in the electric power load on the fan 114. The airflow velocity view 704 shows that, for similar reasons, a relatively low airflow velocity is provided in the cylindrical portion 308, and that irregular airflow velocity is provided through the planar portion 600. The turbulence side view 706 and the turbulence perspective view 708 show the amount of turbulence in the airflow pathway 124. In particular, a high amount of turbulence, corresponding to a high air velocity, is shown in the planar portion 600.

FIG. 8 shows a smoothed transition between the cylindrical portion 308 and the planar portion 600, provided by a curved surface 850 provided between the cylindrical portion 308 and the planar portion 600. FIG. 8 shows a table 800, a pressure view 802 of air pressure in the airflow pathway 124, an airflow velocity view 804 showing the velocity of airflow through the airflow pathway 124, a turbulence side view 806 showing turbulence in the airflow pathway 124 from a side view of the airflow pathway 124, and a turbulence perspective view 808 showing turbulence in the airflow pathway 124 from a perspective view.

The pressure view 802 shows that a relatively-uniform and relatively low pressure is provided throughout the airflow pathway 124 in the embodiment of FIG. 8, relative to the pressure shown in the pressure view 702 in FIG. 7. This may allow for lower power consumption of the fan 114. The pressure in the cylindrical portion 308 may be slightly higher, but not significantly higher, than the pressure in the planar portion 600. The airflow velocity view 804 shows increased velocity at the curved surface 850, with a relatively-consistent and relatively-low airflow rate across the planar portion 600. As indicated in the table 800, the mean exit velocity of the embodiment of FIG. 8 is substantially lower than the mean exit velocity of the embodiment of FIG. 7. The turbulence views 806, 808 show turbulence starting at the curved surface 850 and decreasing as air flows along the planar portion 600.

FIG. 9 shows the cylindrical portion 308 oriented at an obtuse angle (indicated as θ in FIG. 9) relative to the planar portion 600. The obtuse angle θ can be any angle between 90 degrees and 180 degrees, and may preferably be a range between approximate 130 degrees and approximately 150 degrees (e.g., approximately 135 degrees). FIG. 9 shows a table 900, a pressure view 902 of air pressure in the airflow pathway 124, an airflow velocity view 904 showing the velocity of airflow through the airflow pathway 124, a turbulence side view 906 showing turbulence in the airflow pathway 124 from a side view of the airflow pathway 124, and a turbulence perspective view 908 showing turbulence in the airflow pathway 124 from a perspective view.

Due to the angle of the cylindrical portion 308 relative to the planar portion 600, the pressure view 902 shows that the air pressure in the cylindrical portion 308 is relatively low as compared to the embodiment of FIG. 7, while the increase in velocity at the intersection of the cylindrical portion 308 and the planar portion 600 as shown by the airflow velocity view 904 is lower than in the embodiments of FIGS. 7 and 8. The turbulence views 906, 908 show that similar turbulence is created in the planar portion 600 in the example of FIG. 9 as in the example of FIG. 8. This turbulence may help to disrupt the surface of the first membrane 130 and the second membrane 132 in a way that enhances evaporation. The mean exit velocity and mean surface velocity shown in the table 900 of the example of FIG. 9 are slightly lower than those shown in the example of table 800 of FIG. 8.

Figure 10:
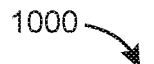
FIG. 10 is a graph of results comparing evaporation in canisters corresponding to FIGS. 7-9, according to an example experiment and example embodiments.
Figure 10:
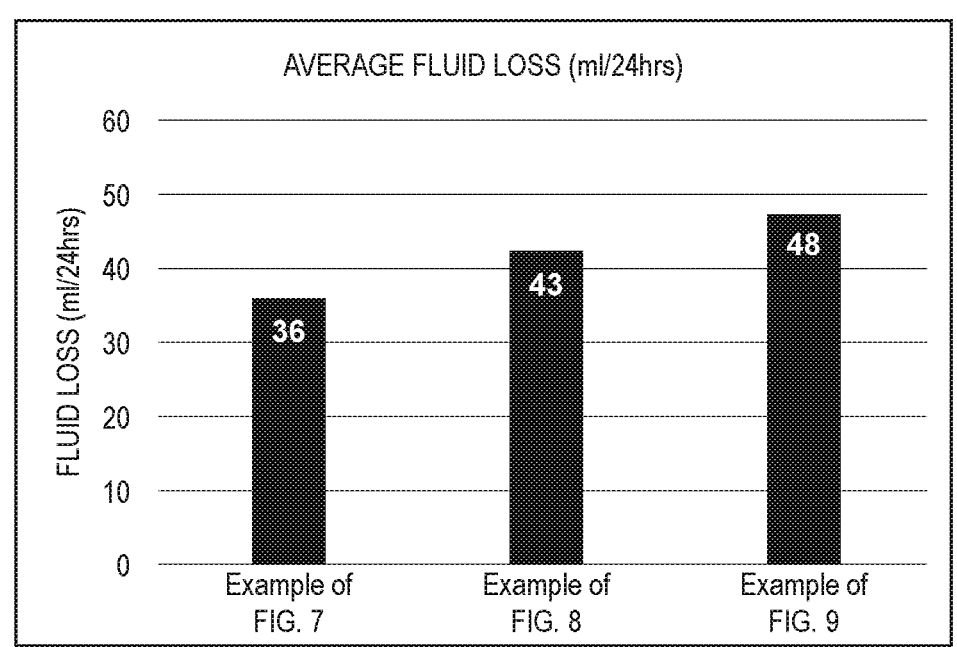

Referring now to FIG. 10, a table 1000 comparing amounts of evaporation from the canister 104 provided by the example embodiments of FIGS. 7-9 according to an example experiment is shown. As shown in FIG. 10, the example of FIG. 8 (i.e., an embodiment of the canister 104 in which a curved surface 850 is provided at the intersection of the cylindrical portion 308 and the planar portion 600) provides for more evaporation than the example of FIG. 7, while the example of FIG. 9 (i.e., an embodiment where cylindrical portion 308 is at an obtuse angle relative to the planar portion 600) provides for more evaporation than the example of FIG. 9. The experiment of FIG. 10 may be conducted with fan speed and/or power consumption as a fixed value across the three embodiments, such that the example of FIG. 9 provides the most efficient evaporation relative to power consumption of the fan 114. FIG. 10 shows that any of the embodiments herein can provide actively enhanced evaporation of water from the canister 104 to extend the lifetime of the canister 104.

As utilized herein, the terms "approximately," "about," "substantially," and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the disclosure as recited in the appended claims.

It should be noted that the term "exemplary" and variations thereof, as used herein to describe various embodiments, are intended to indicate that such embodiments are possible examples, representations, and/or illustrations of possible embodiments (and such terms are not intended to connote that such embodiments are necessarily extraordinary or superlative examples).

The term "coupled," as used herein, means the joining of two members directly or indirectly to one another. Such joining may be stationary (e.g., permanent or fixed) or moveable (e.g., removable or releasable). Such joining may be achieved with the two members coupled directly to each other, with the two members coupled to each other using a separate intervening member and any additional intermediate members coupled with one another, or with the two members coupled to each other using an intervening member that is integrally formed as a single unitary body with one of the two members. Such members may be coupled mechanically, electrically, and/or fluidly.

References herein to the positions of elements (e.g., "top," "bottom," "above," "below," etc.) are merely used to describe the orientation of various elements in the FIGURES. It should be noted that the orientation of various elements may differ according to other exemplary embodiments, and that such variations are intended to be encompassed by the present disclosure.

What is claimed is:

1. A canister for use with a wound therapy system, comprising:
first and second compartments configured to receive and contain wound exudate;
an airflow pathway comprising:
a planar region positioned between the first compartment and the second compartment;
an inlet extending from a first end of the planar region at an obtuse angle relative to the planar region; and
an outlet at a second end of the planar region.

2. The canister of claim 1, wherein the first compartment is separated from the airflow pathway by a first filter configured to:
allow water molecules to pass from the first compartment to the airflow pathway; and
prevent contaminants from passing from the first compartment to the airflow pathway.

3. The canister of claim 2, wherein the first filter comprises a polyether urethane film.

4. The canister of claim 3, comprising a rigid structure defining the first and second compartments and formed of a thermoplastic polyurethane resin.

5. The canister of claim 4, wherein the rigid structure is ultrasonically welded to the polyether urethane film.

6. The canister of claim 2, wherein the first filter comprises a film having a high moisture vapor transmission rate.

7. The canister of claim 6, wherein the high moisture vapor transmission rate is in a range between 2000 and 5000 g/m²/day.

8. The canister of claim 1, wherein the inlet is cylindrical.

9. The canister of claim 1, wherein the inlet is formed to match a cross-sectional shape of a fan.

10. The canister of claim 1, wherein the inlet widens proximate the planar region to reduce turbulence and backpressure in the airflow pathway.

11. The canister of claim 1, further comprising a curved wall providing a smooth transition from the inlet to the planar region.

12. The canister of claim 1, wherein the obtuse angle is in a range between 130 degrees and 150 degrees.

13. The canister of claim 1, wherein the inlet has a screw-type form configured to provide rotation of airflow therethrough.

14. A therapy system, comprising:
a dressing configured to be sealed over a wound site;
a negative pressure source configured to draw a negative pressure at the dressing and cause wound exudate to move out of the dressing;
a canister configured to be placed in fluid communication with the dressing, the canister comprising:
first and second compartments configured to receive and retain the wound exudate from the dressing; and
an airflow pathway comprising:
a planar region positioned between the first compartment and the second compartment;
an inlet extending from a first end of the planar region at an obtuse angle relative to the planar region; and
an outlet at a second end of the planar region; and
an air mover aligned with the inlet and configured to force air through the airflow pathway to facilitate transfer of moisture from the wound exudate out of the first and second components.

15. The therapy system of claim 14, comprising a housing, wherein the air mover and the negative pressure source are installed in the housing, and wherein the canister is configured to be selectively and removeably coupled to the housing.

16. The therapy system of claim 15, further comprising a battery installed in the housing and configured to power the air mover and the negative pressure source.

17. The therapy system of claim 14, further comprising a controller configured to control the air mover to operate in a pulsing pattern.

18. The therapy system of claim 14, wherein the first and second compartments are separated from the airflow pathway by a film material configured to:
allow water molecules to pass from the first and second compartments to the airflow pathway; and
prevent contaminants from passing from the first and second compartments to the airflow pathway.

19. A method of manufacturing a canister for a wound therapy device, comprising:
providing first and second rigid structures formed of a polyurethane resin;
providing first and second filters formed of a polyether urethane film;
ultrasonically welding the first rigid structure to the first filter;
ultrasonically welding the second rigid structure to the second filter; and
ultrasonically welding the first rigid structure to the second rigid structure such that a planar airflow pathway is defined between the first filter and the second filter.

20. The method of claim 19, comprising forming the first and second filters such that the first and second filters are configured to allow water molecules to pass across the first and second filters.

* * * * *